(12) United States Patent
Melnikov et al.

(10) Patent No.: US 8,052,747 B2
(45) Date of Patent: Nov. 8, 2011

(54) HEART VALVE PROSTHESIS WITH TURN STOPS

(76) Inventors: Alexandr Petrovich Melnikov, Moscow (RU); Denis Alexandrovich Melnikov, Moscow (RU)

( * ) Notice: Subject to any disclaimer, the term of this patent is extended or adjusted under 35 U.S.C. 154(b) by 129 days.

(21) Appl. No.: 12/158,584

(22) PCT Filed: Dec. 8, 2006

(86) PCT No.: PCT/RU2006/000658
§ 371 (c)(1),
(2), (4) Date: Jun. 20, 2008

(87) PCT Pub. No.: WO2007/075121
PCT Pub. Date: Jul. 5, 2007

(65) Prior Publication Data
US 2008/0300676 A1 Dec. 4, 2008

(30) Foreign Application Priority Data
Dec. 23, 2005 (RU) ................. 2005140363

(51) Int. Cl.
*A61F 2/24* (2006.01)
(52) U.S. Cl. ........................... 623/2.1; 623/2.12
(58) Field of Classification Search ............ 623/2.1, 623/2.12–2.2, 2.22
See application file for complete search history.

(56) References Cited

U.S. PATENT DOCUMENTS

| 4,274,437 | A | 6/1981 | Watts |
| 6,007,577 | A | 12/1999 | Vanney et al. |
| 6,176,877 | B1 | 1/2001 | Buchanan et al. |
| 6,719,790 | B2 | 4/2004 | Brendzel et al. |

FOREIGN PATENT DOCUMENTS
RU 2066984 9/1996

*Primary Examiner* — Thomas J Sweet
*Assistant Examiner* — Matthew Schall
(74) *Attorney, Agent, or Firm* — Rader, Fishman & Grauer PLLC (57) ABSTRACT

A heart valve prosthesis disclosed in two- and three-leaflet versions includes a ring-shaped body, leaflets, and leaflet turn stops. For the two-leaflet version, the stops represent two pairs of prominences located on a body end surface facing the blood down-flow. The first pair has internal surfaces, at least partially made flat, adapted to interact with flat sections of the leaflets to restrict the return blood flow in the closed position. The first pair is equipped with at least two rests interacting with a leaflet top surface facing the blood down-flow in its open position determining a leaflet turning angle. Each prominence of the second pair is located opposite a portion of the lateral surface of the corresponding leaflet most distant from a leaflet central surface and can interact with its internal surface with that part of the lateral surface during opening of the heart valve prosthesis.

27 Claims, 11 Drawing Sheets

HEART VALVE PROSTHESIS WITH TURN STOPS

CROSS-REFERENCE TO RELATED APPLICATIONS

This application claims the priority of PCT application PCT/RU2006/000658 of Dec. 8, 2006, published as WO 2007/075121 A1, and of application 2005140363 filed in Russia on Dec. 23, 2005, the entire contents of which are incorporated by reference herein.

BACKGROUND OF THE INVENTION

1. Field of the Invention

The present invention relates to medicine, and in particular, to cardiovascular surgery and is designed for replacement of affected natural heart valves during cardiac surgery.

2. Description of the Related Art

There are many designs of heart valves prostheses used for replacement of natural valves: ball, frameless, single leaflet, bi-leaflet, tri-leaflet prostheses. Widely used implanted frame prostheses are very reliable and ensure satisfactory hemodynamics, appropriate improvements reduce acoustic noises, anxiety of patients, increase the time of continuous operation. Standard prostheses include a ring-shaped body providing a channel for the flow of blood. Installed in the body is one or more leaflets configured for the alternation of an open position for the passage of a direct flow of blood and a closed position for the closure of the channel and restriction of a reverse flow of blood. In addition, the heart valve prosthesis contains a coupling arrangement for the connection of the valve body with surrounding heart tissues. Basically, this arrangement is made in the form of a cuff which is sewed to the heart tissues and envelopes the lateral surface of the prosthesis valve body.

Research and engineering activity have been permanently carried out for the creation of new designs of valve prostheses and modernization of existing ones by means of improvement of their features.

Efforts to increase the efficiency of heart valve prostheses are continued. The efficiency of the heart valve prosthesis is determined by the area of the flow section when the leaflets are in the open position. The valve body of the prosthesis sewed in with the help of the cuff into place of a removed natural valve has a certain thickness reducing the flow section, the leaflets exhibiting resistance to the flow and partially closing a passage opening, especially when positioned centrally. The effective area of the valve flow section is thus reduced, which is one of the main critical factors of the heart valve prostheses. This is particularly dangerous in valves of small diameters.

Known from the prior art have been artificial heart valves which eliminate this disadvantage to a certain extent—these are the valves with an increased flow section and central positioning of leaflets upon the opening of the valve (see e.g. U.S. Pat. Nos. 6,007,577, 6,176,877, 6,719,790). The increase of the flow section in these prostheses is achieved by making the valve body with a flow section one size up (by approx. 2 mm) as compared with a regular valve, a cuff of a special design ensuring the installation of such valve into a position over the excised natural one. Thus, the thickness of the prosthesis body does not change the flow section of the valve, which remains equal to that the natural valve used to have.

However, a problem of hemodynamics distortion stays unsolved for such artificial valves. Indeed, the leaflets in the open position of the valve stay in the central area of the velocity profile distorting it and reducing the blood flow velocity through the valve.

A number of designs is known (see U.S. Pat. No. 4,274,437, RU 2066984) where the main flow section is provided in the center. It is obvious in such a design that the central part of the flow through the valve remains weakly disturbed and the distortions caused by the leaflets are minimal. However, these valves have no practical application in surgery because of low reliability and high probability of the falling out of the leaflets. As it turned out, the central problem was designing such leaflet traveling stops, which could reliably hold the leaflets during the whole life of the valve and contribute to its continuous operation.

So a need for a new design of the heart valve prosthesis combining the reliability and undistorted hemodynamics of the blood flow is obvious.

The closest analog for this invention is an artificial heart valve (RU 2066984) containing a ring-shaped body and two leaflets placed therein with a possibility of turning between top and bottom stops in relation to the blood flow and of forming the main zone of the flow section in the center, the zone being limited by round sections of inner walls of the body and bottom edges of the leaflets in relation to the blood flow, the bottom stops of each leaflet including a pair of half-axles installed near the periphery of the valve section and the top stop of each leaflet including a rest, the end of which is located in a groove of the rectangular cross-section made on a leaflet peripheral edge facing the rest.

SUMMARY OF THE INVENTION

This invention is directed to the solution of a problem of creating an artificial heart valve that would eliminate disadvantages of the known analogs, namely having its main zone of the flow at the center and also having such a design of stops, which could ensure reliability and long continuous life of the valve.

Technical result obtained with the use of this invention consists in increasing the reliability of holding the leaflets during the traveling.

The technical result is obtained thanks to that in the heart valve prosthesis containing a ring-shaped body, leaflets installed inside the body and configured to be able to turn and form a main zone of the flow section in the center, and leaflet turn stops, the leaflet turn stops include two pairs of prominences located on an end surface of the body facing the blood down-flow, the first pair of the prominences having an internal surface, at least a part of which is made flat and which is configured to be able to interact with flat sections of the leaflets to restrict the return flow of blood in the closed position thereof, prominences on opposite sides having guiding surfaces interacting with corresponding bearing surfaces of the lateral surface of the leaflets as they turn, generating lines of the guiding surface of the prominences being inclined toward their internal surface and having a shape corresponding to the turn trajectory of the bearing surfaces of the leaflets determining the axes of their turning upon the opening and closing of the prosthesis, each prominence of the second pair being located opposite a part of the lateral surface of the corresponding leaflet, which is the most distant from the central surface, and being configured to be able to interact by its internal surface with the part of the leaflet's lateral surface during opening the heart valve prosthesis, the leaflet turn stops being provided with at least two rests interacting with the surfaces of the leaflets, which face the down-flow of blood in their open position, defining the turning angle of the leaflets.

The technical result can be increased if the mentioned flat sections of the leaflets are located on the lateral surface of each leaflet from two diametrically opposite sides and have a possibility of interaction with the corresponding flat surface of the leaflet turn stop in closed position, each flat section of the leaflet ending as a bearing surface, generating lines of which are inclined towards the flat surfaces, the bearing surfaces of the leaflets having a possibility of interaction with the corresponding guiding surfaces of the leaflet turn stops during the opening and closing of the heart valve prosthesis.

In the first embodiment of the leaflet turn stops, the first pair of prominences is equipped with four rests which are located in pairs on the internal surface of the prominences from a side facing the blood down-flow.

In another embodiment, the first pair of prominences is equipped with four rests which are located in pairs on the opposite lateral sides of the first pair of prominences from a side facing the blood down-flow.

The third embodiment is characterized by that the turn stops are provided with two rests, each of which is located on the internal surface of the second pair from side facing the blood down-flow.

The internal surface of an opening of the ring-shaped body is made as a lateral surface of the circular cylinder and limited by two flat ends facing blood up-flow and down-flow, respectively.

Two hollows are made on the end facing the down-flow of blood, the surfaces of each hollow serving for interaction with the part of the lateral surface of the corresponding leaflet, which is the most distant from the central surface, upon opening and closing the prosthesis and forming a limited return blood flow in its closed position.

A circular groove for fastening of an inserted cuff can be made on an external side of the body.

The external surface of each leaflet facing the blood down-flow is made at least partially concave, and the external surface of each leaflet facing the blood up-flow is made at least partially convex, generating lines of the mentioned parts of the surfaces are inclined to the central surface of the leaflet.

The external surface of each leaflet facing the blood down-flow is made at least partially concave, and the external surface of each leaflet facing the blood up-flow is made at least partially convex, axes of symmetry of the mentioned parts of surfaces are inclined to the central axis of the ring-shaped body.

The convex and concave parts of the external surfaces of the leaflets represent lateral surfaces of the circular cylinder inclined relative the central axis of the heart valve prosthesis.

All valve parts are made of pyrolytic carbon.

In addition, the technical result is obtained thanks to that in the heart valve prosthesis comprising a ring-shaped body, three leaflets installed inside the body and configured to be able to turn and form a main zone of the flow area in the center of the body opening, and leaflet turn stops, the leaflet turn stops including two triplets of prominences located on the end surface of the body facing the blood down-flow, the first triplet of prominences having on their opposite lateral sides guiding surfaces which interact with corresponding bearing surfaces of the lateral surface of leaflets upon the opening and closing of the prosthesis, each prominence of the second triplet of prominences being located opposite a corresponding leaflet lateral surface portion, which is the most distant from the central surface, and being configured to be able to interact by its internal surface with the leaflet lateral surface portion during the opening of the heart valve prosthesis, the leaflet turn stops being provided with at least three rests interacting with leaflet surfaces facing the blood down-flow in the open position of the leaflets determining the turning angle thereof.

BRIEF DESCRIPTION OF THE DRAWINGS

The character of the invention will be more clear from a description given below with references to the drawings, in which.

A structure of a tri-leaflet valve is shown in FIGS. 16-19, where.

DETAILED DESCRIPTION OF THE INVENTION

Figure 5:
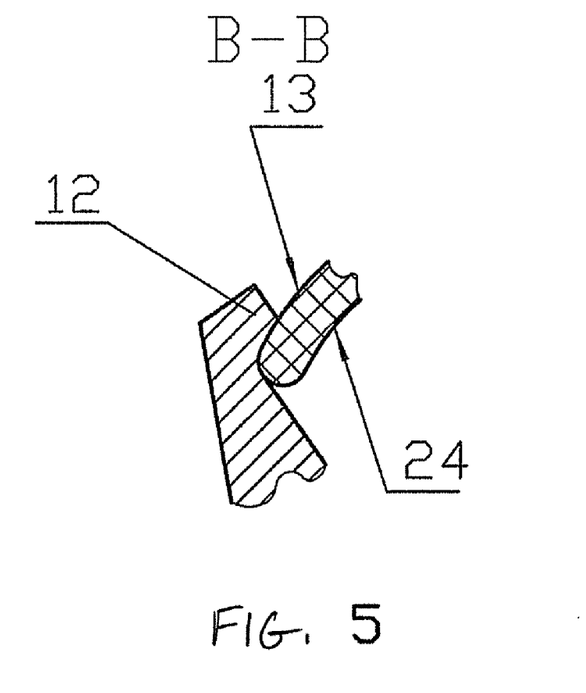
Figure 9:
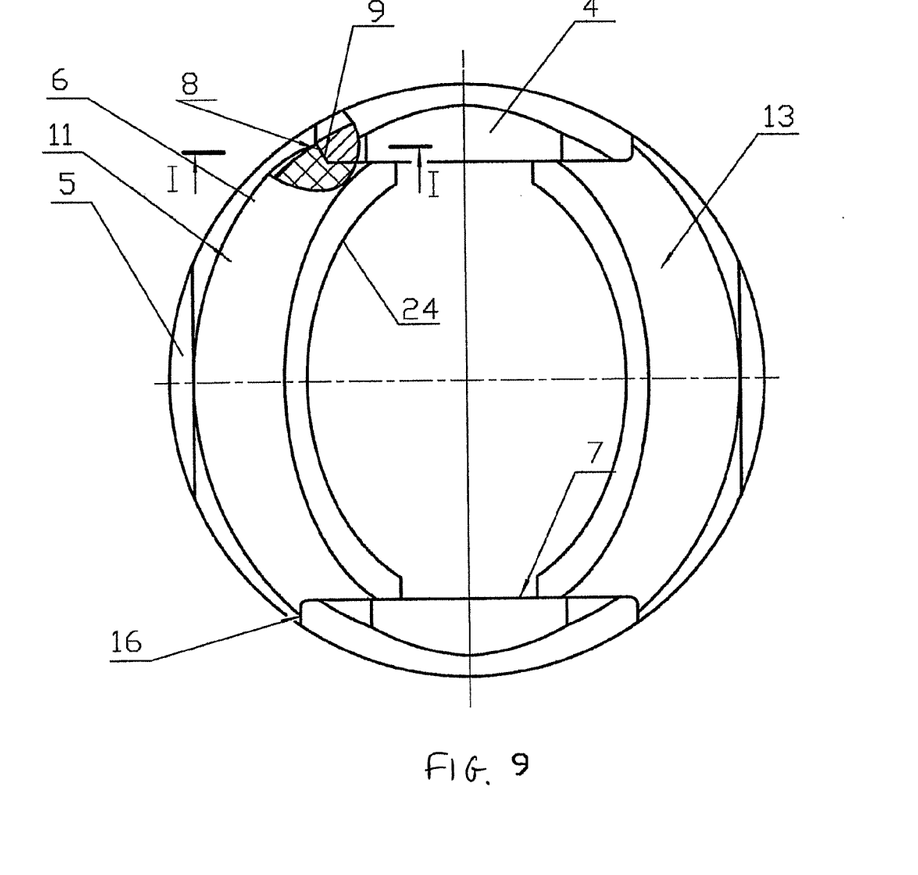
Figure 10:
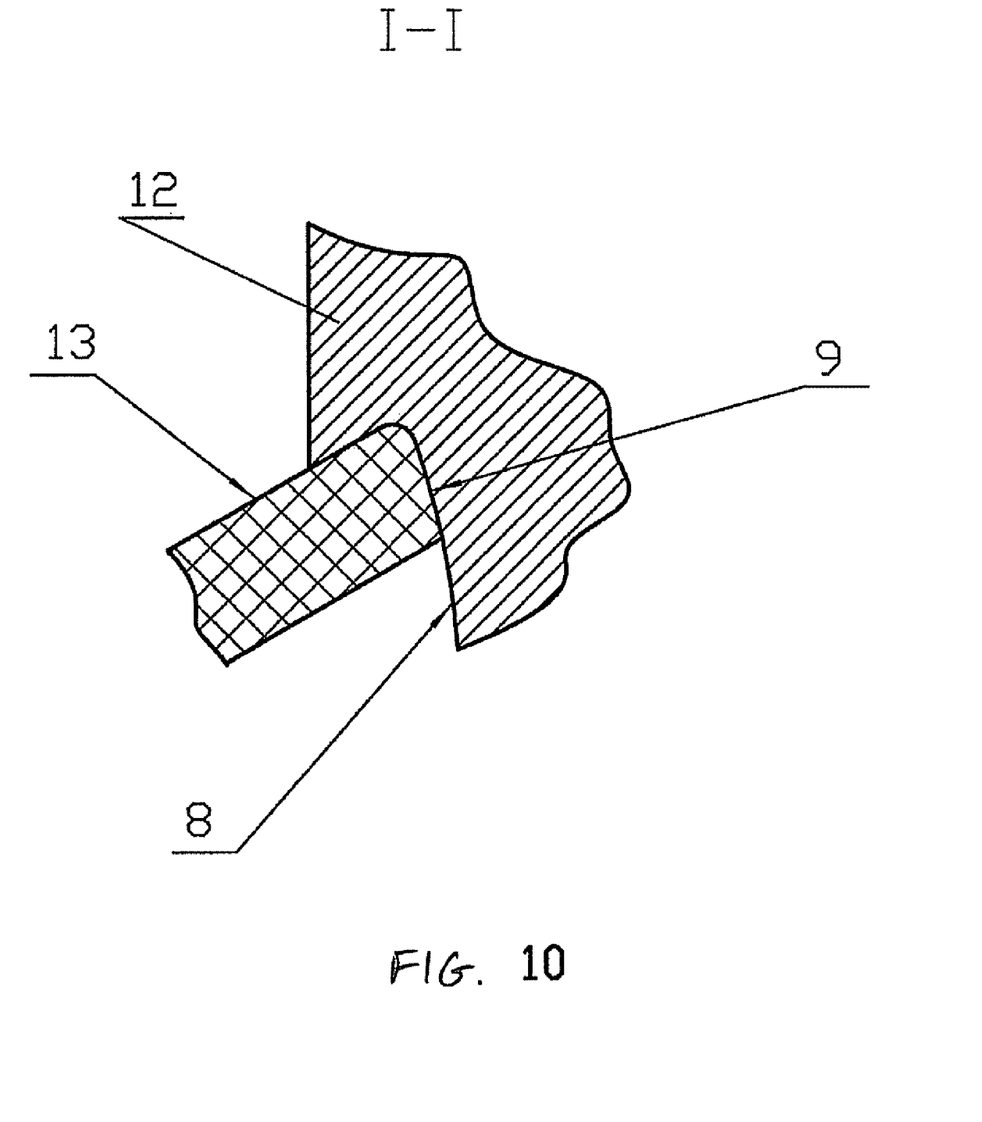
Figure 15:
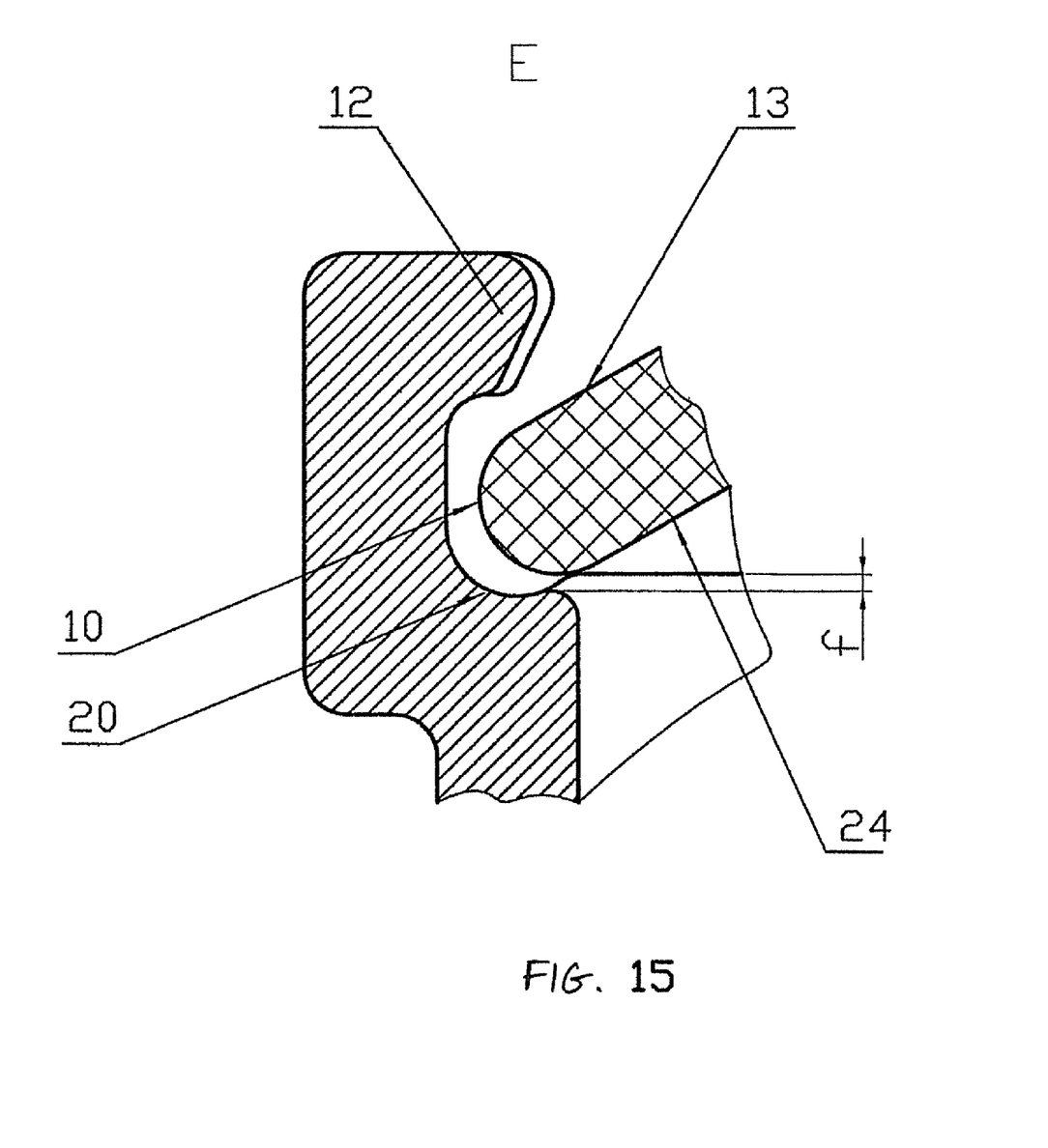
Figure 18:
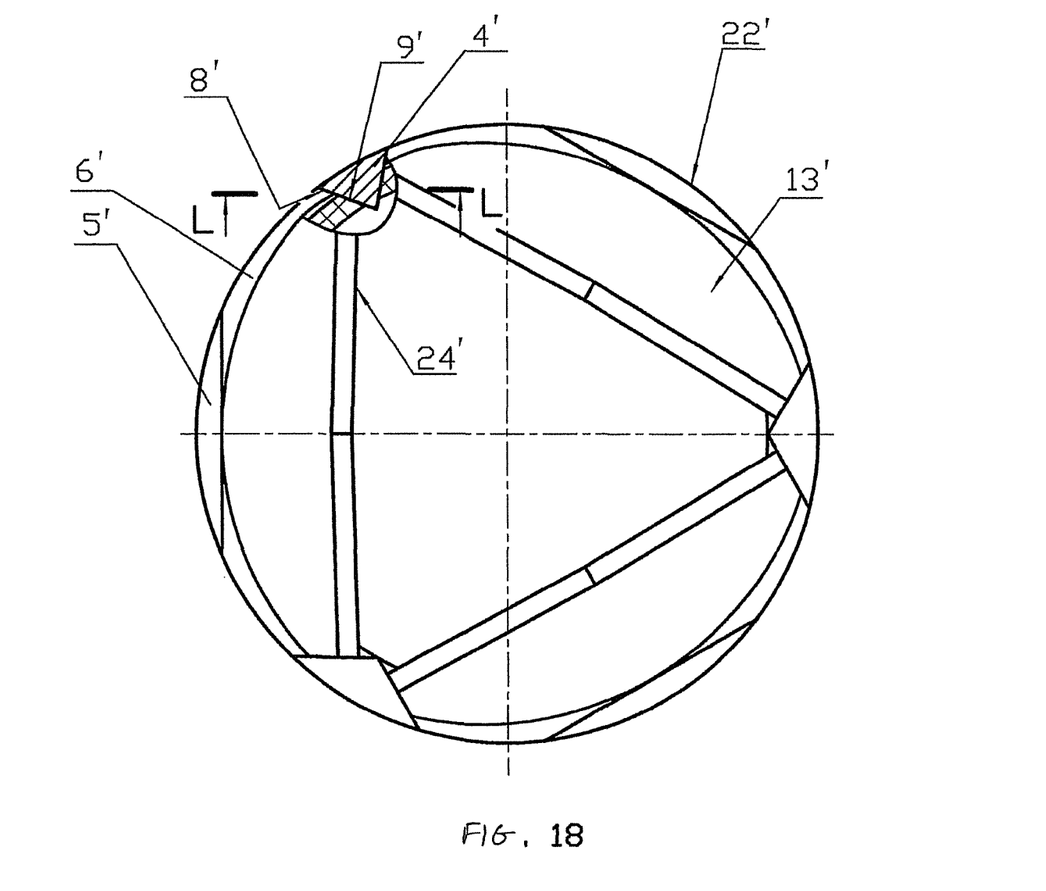
Figure 19:
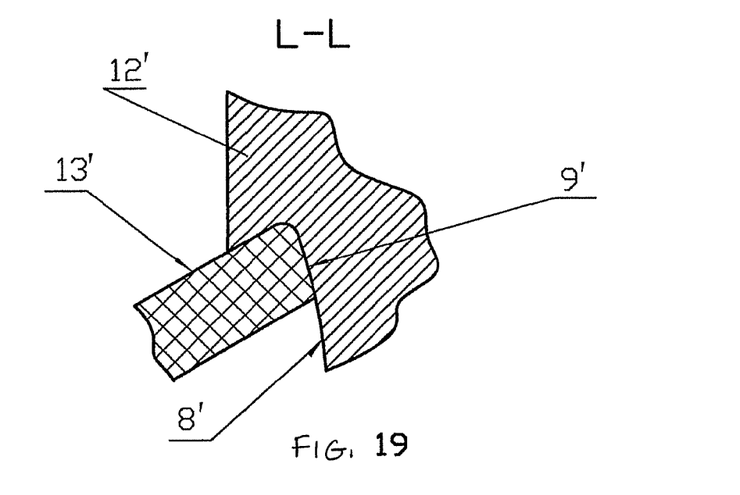

A heart valve prosthesis 1 contains a ring-shaped body 2 made of pyrocarbon. The body 2 has two or three leaflets 3 also made of pyrocarbon and installed in the body 2 outside a body opening 17, the leaflets 3 being configured to be able to turn and form a main zone of the flow section at the center. Leaflet turn stops 18 are made as integral parts of the body and include two pairs of prominences—a first pair 4 of prominences and a second pair 5 of prominences located on an end surface 6 of the body 2 facing the blood down-flow (indicated with a down arrow in the drawings). In the version of a tri-leaflet valve, the stops include two triplets of the prominences accordingly. A design version of the bi-leaflet valve will be described further for the sake of simplicity. The first pair 4 of the prominences has an internal surface 7, a portion of which is made flat and interacts with flat sections of the leaflets 3 for restricting the reverse flow of blood in the closed position. On their opposite lateral sides, the prominences 4 have guiding surfaces 8 interacting with bearing surfaces 9 of a lateral surface of the leaflets 3 when the leaflets turn. Generating lines of the guiding surface of the prominences 4 and 5 are inclined to their internal surface and have a shape corresponding to a turn trajectory of the bearing surfaces 9 of the leaflets 3 defining the axes of their turning upon opening and closing the prosthesis 1. Each prominence 5 of the second pair is located opposite a portion 10 of the lateral surface 11 of the corresponding leaflet 3, which is the most distant from the central surface, and is able to interact by its internal surface with the above-mentioned portion of the lateral surface 11 of the leaflet 3 during opening the heart valve prosthesis 1. The turn stops 18 of the leaflets 3 are equipped with rests 12 interacting with a top (for the purposes of FIGS. 5, 9, 10, 15, 18, and 19) surface 13 of the leaflet 3 facing the blood down-flow in its open position defining the turning angle of the leaflet 3.

Flat portions 14 of the leaflets 3 are located on the lateral surface of each leaflet 3 from two diametrically opposite sides, these portions interacting with a corresponding flat surface 15 of the turn stop of the leaflet 3 in the closed position. Each of the flat portions 14 of the leaflet 3 ends in the bearing surface 9, generating lines of which are inclined towards the flat surfaces 15. The bearing surfaces 9 of the leaflets interact with the corresponding guiding surfaces 8 of the turn stops 18 of the leaflets 3 during opening and closing of the heart valve prosthesis 1.

Figure 1:
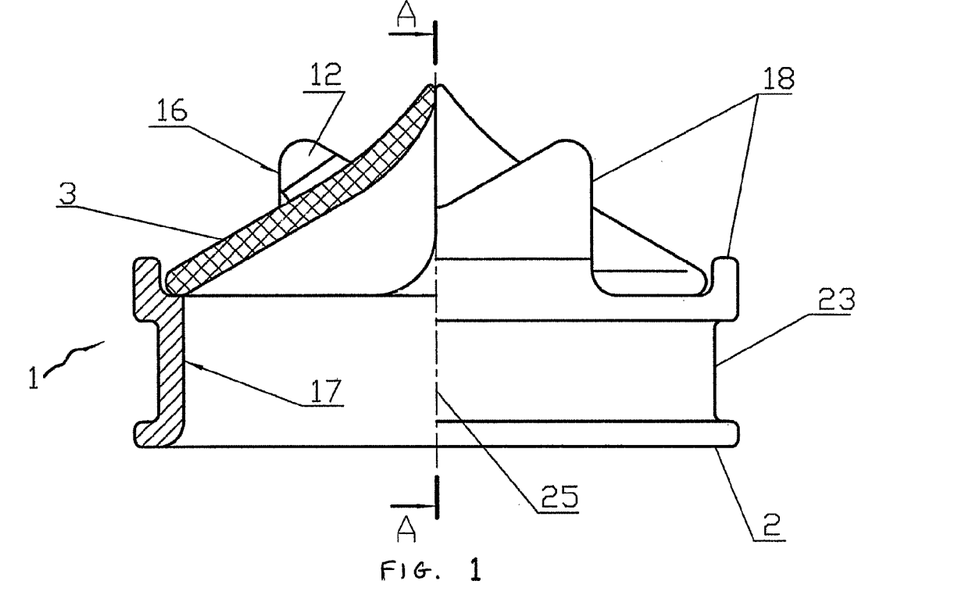
FIGS. 1-5 show a valve implementing the first embodiment of leaflet turn stops and depict respectively: a front view of the valve with closed leaflets (FIG. 1), the same with open leaflets (FIG. 2), a cross-sectional view (FIG. 3) along the line A-A in FIG. 1, a top view (FIG. 4), and a cross-sectional view (FIG. 5) along the line B-B in FIG. 2 showing the interaction of the rest and the leaflet in its open position.
Figure 2:
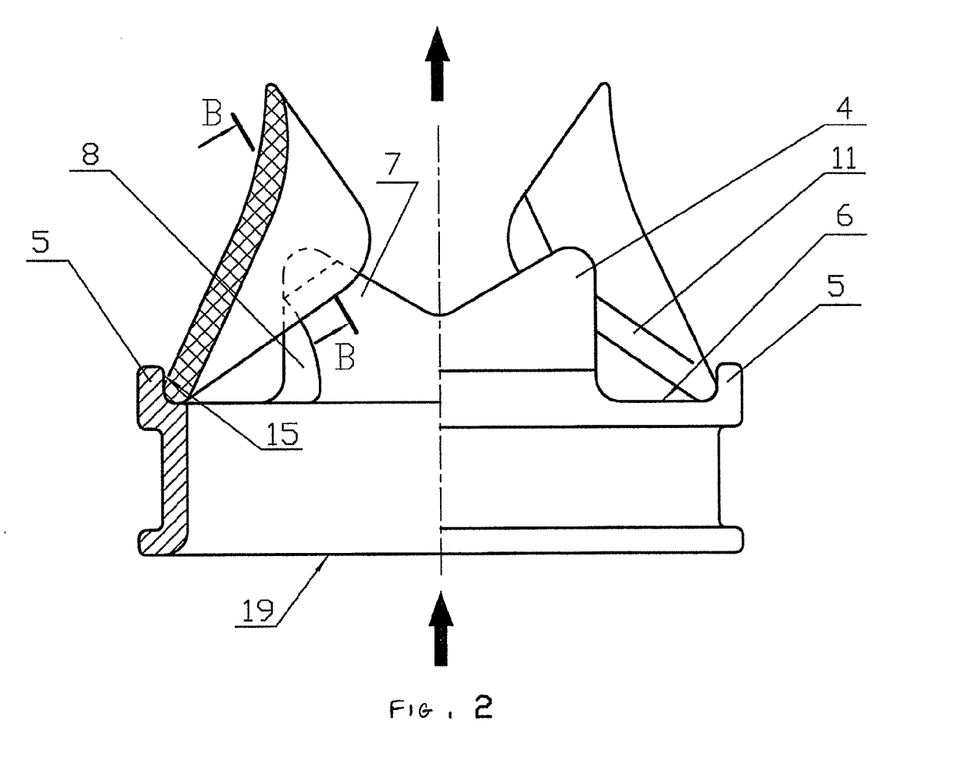
Figure 3:
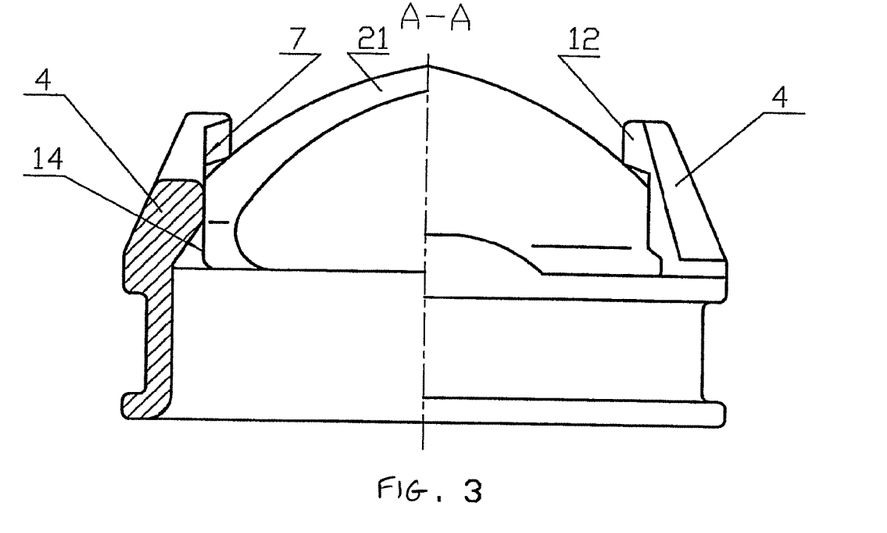
Figure 4:
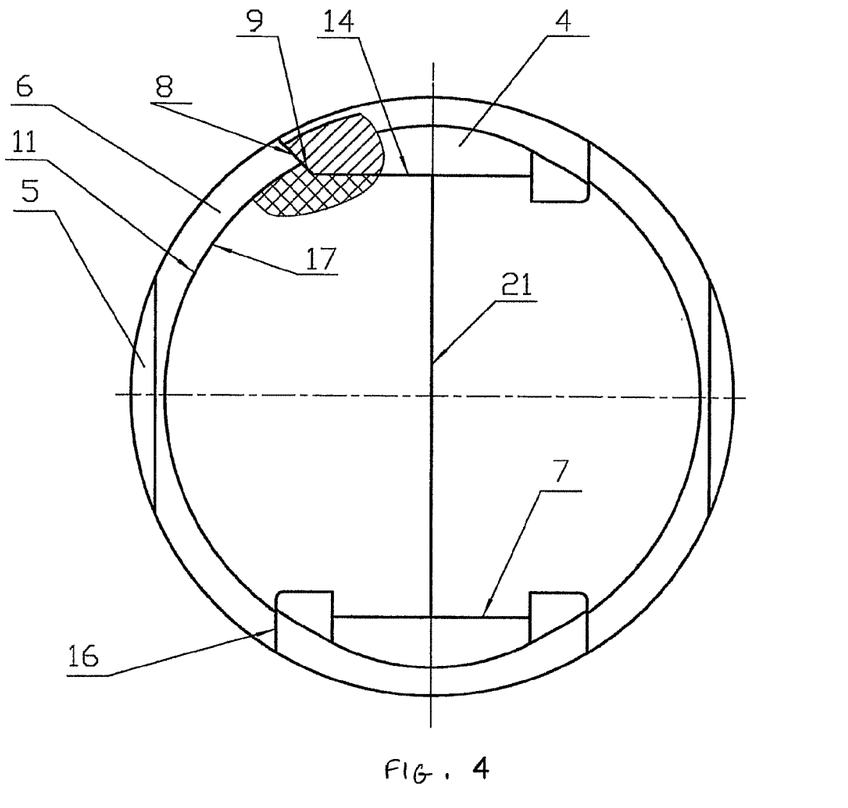

In the first embodiment of the turn stops 18 (FIGS. 1-5), the first pair of prominences 4 is equipped with four rests 12 which are located in pairs on the internal surface 7 of the prominences 4 from the side facing the blood down-flow.

Figure 6:
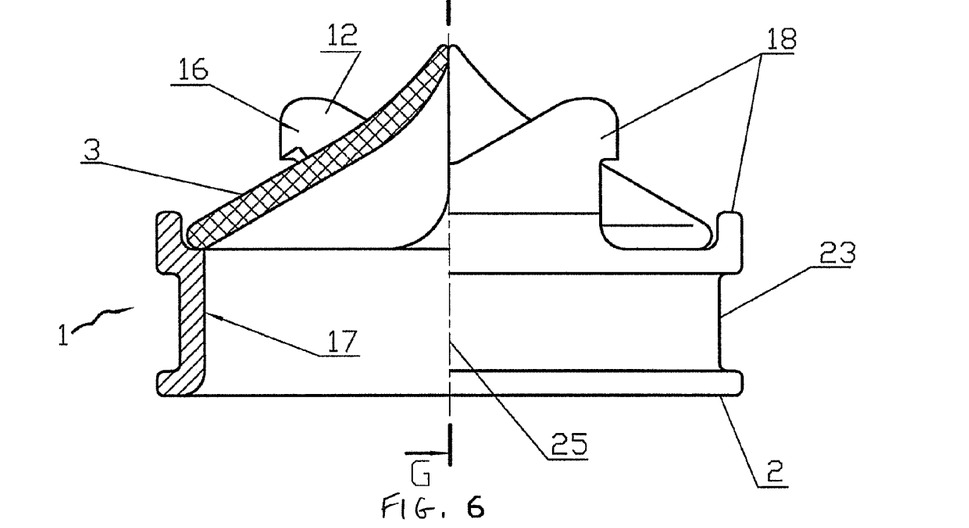
FIGS. 6-10 illustrate the valve according to the second embodiment of leaflet turn stops and show respectively: a front view of the valve with closed leaflets (FIG. 6), the same with open leaflets (FIG. 7), a cross-sectional view (FIG. 8) along the line G-G in FIG. 6, a top view (FIG. 9), and a cross-sectional view (FIG. 10) along the line I-I in FIG. 9 showing the interaction of the rest and the leaflet.
Figure 7:
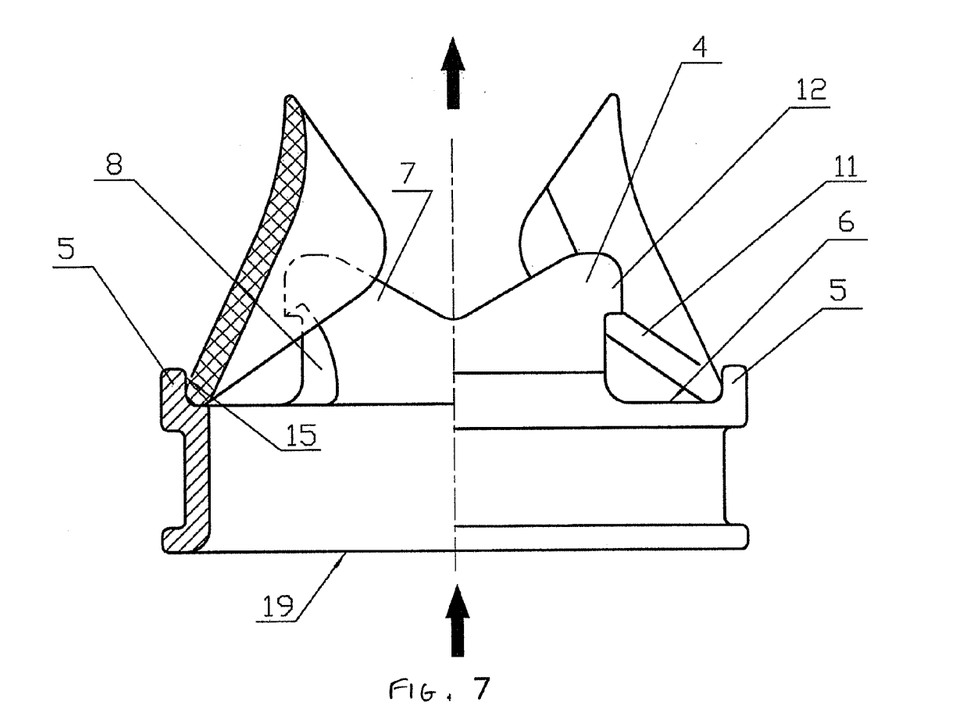
Figure 8:
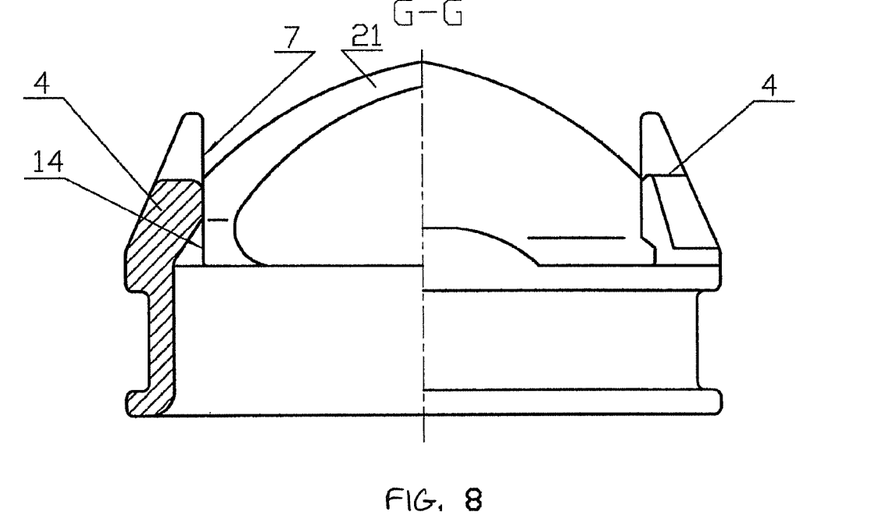

In another embodiment (FIGS. 6-10), the first pair of prominences 4 is provided with four rests 12 which are located in pairs on opposite lateral sides 16 of the first pair of prominences 4 from the side facing the blood down-flow.

Figure 11:
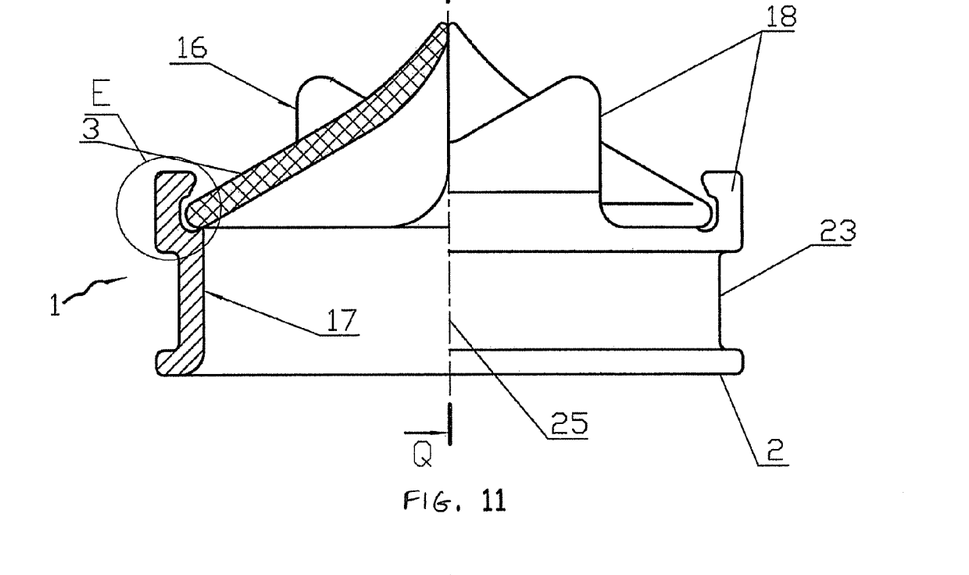
FIGS. 11-15 present the valve in accordance with the third embodiment of leaflet turn stops, specifically: a front view of the valve with closed leaflets (FIG. 11), the same with open leaflets (FIG. 12), a cross-sectional view (FIG. 13) along the line Q-Q in FIG. 11, a top view (FIG. 14), an enlarged view (FIG. 15) of area E from FIG. 11 showing the interaction of hollows of the rest and the leaflet.
Figure 12:
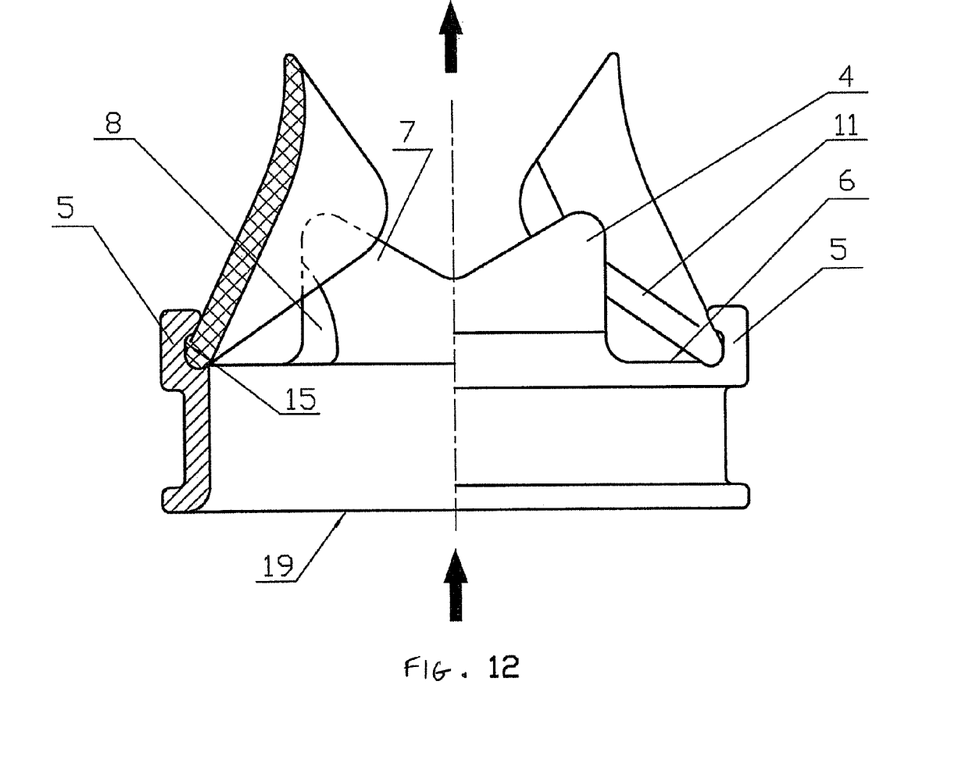
Figure 13:
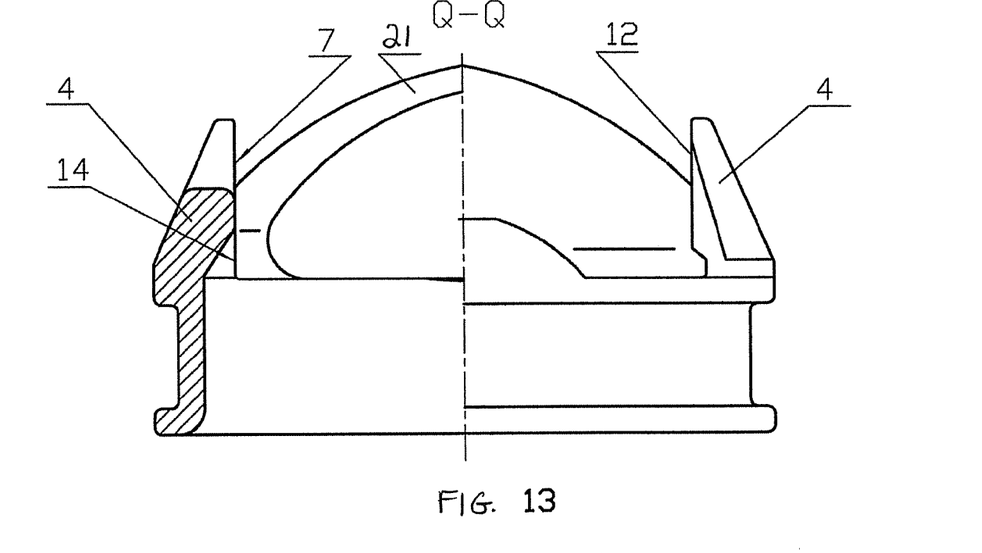
Figure 14:
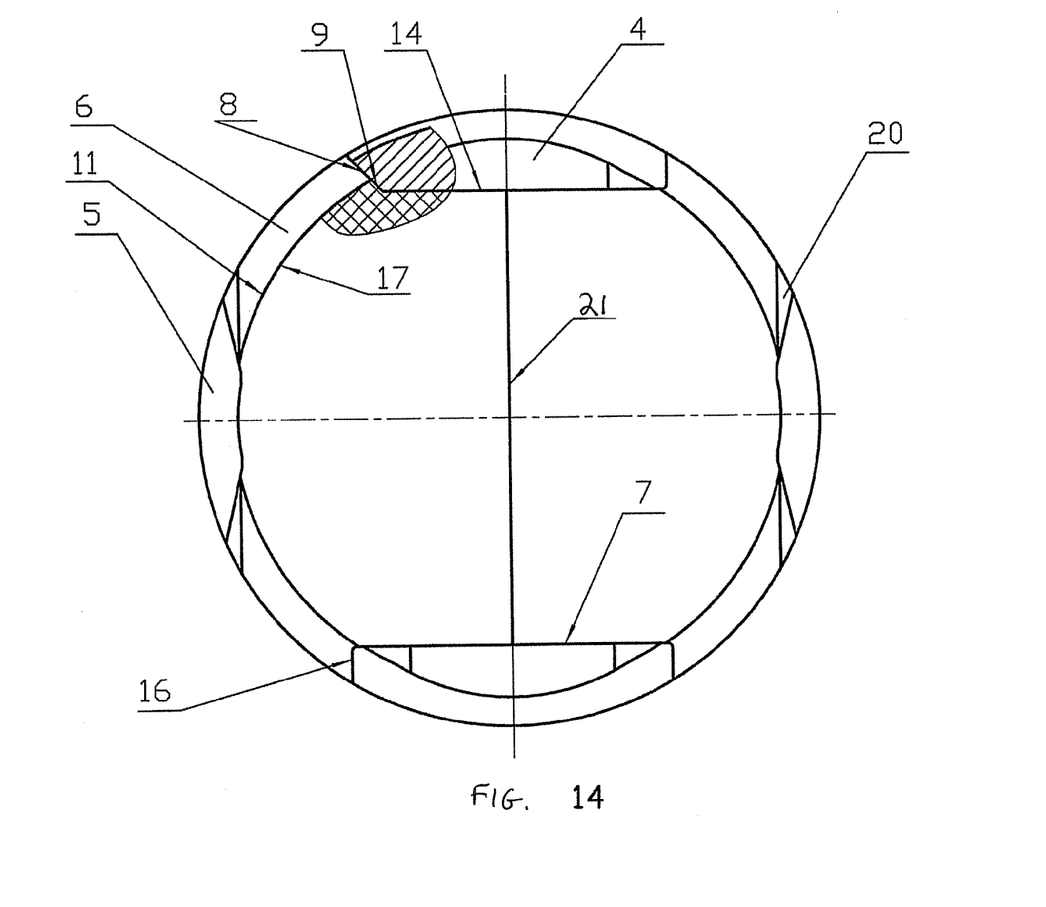

The third embodiment (FIGS. 11-15) has two rests 12 of the turn stops 18, each of the rest 12 being located on the internal surface of the second pair of prominences 5 from the side facing the blood down-flow.

Figure 17:
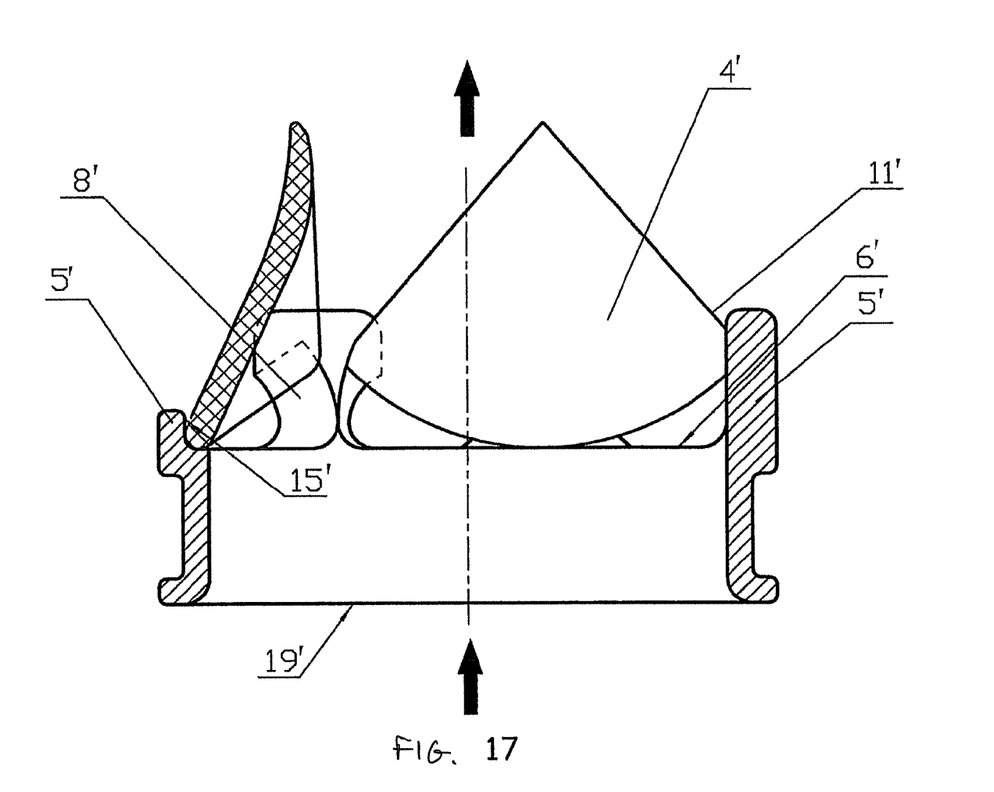

The surface of the opening 17 of the ring-shaped body 2 is made as a lateral surface of the circular cylinder and limited by two flat ends 19 and 6 facing the blood up-flow and down-flow respectively (indicated in FIGS. 2, 7, 12, and 17 with upper and lower thick arrows accordingly).

Two hollows 20 are made on the end 6 facing the blood down-flow. Surfaces of each hollow 20 serve for interaction with the portion 10 of the lateral surface 11 of the corresponding leaflet 3, which is the most distant from a central surface 21, upon opening and closing of the prosthesis 1 and forming of a limited reverse flow of blood in its closed position through a gap f (FIG. 15) between the leaflets 3 and the end surface 6 of the body 2.

A circular groove 23 for fastening of an inserted cuff (not shown) is made on an external surface 22 of the body 2.

The top surface 13 of each leaflet 3 facing the blood down-flow is made at least partially convex. A bottom (for the purposes of FIGS. 5, 9, 10, 15, 18, and 19) surface 24 of each leaflet directed to the upstream flow of blood is made at least partially concave.

The generating lines of the mentioned portions of surfaces are inclined to the central surface 21 of the leaflet 3. The axes of symmetry of the mentioned portions of the surfaces 13 and 24 are inclined to a central axis 25 of the ring-shaped body 2. The convex and concave portions of the surfaces 13 and 24 of the leaflets 3 present lateral surfaces of the circular cylinder inclined relative to the central axis 25 of the heart valve prosthesis 1.

The heart valve prosthesis operates as follows. Upon opening the valve prosthesis 1, the action of the direct flow of blood causes the turning of the leaflets 3 around an imaginary axis defined by the interaction between the bearing surfaces 9 of the leaflets 3 and the guiding surfaces 8 of the first pair of prominences 4. This turn occurs until equilibrium is established, the blood flowing in the forward direction, the central part of the opening 17 of the valve body 2 passing it freely and in its true value. The leaflets are located practically vertically and offer no resistance to the flow. The rests 12 of the turn stops 18 of the leaflets 3 interact with the top surface 13 of the leaflets and reliably hold them in the open position. The convexo-concave making of external surfaces of the leaflets provides opening the valve even further. Upon stopping the forward flow, the leaflets 3 begin to turn and return to their original position as far as their central surfaces 21 contact each other and form in the closed position of the valve prosthesis a limited reverse flow of blood through the gap f between the leaflets 3 and the end surface 6 of the body 2.

Figure 16:
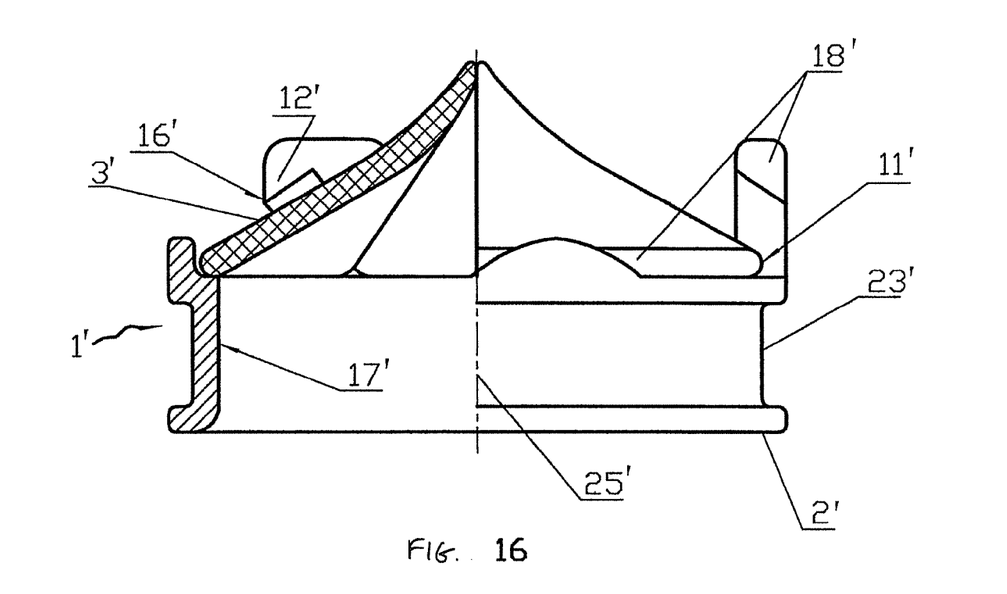
FIG. 16 is a front view of the valve with closed leaflets, FIG. 17—a front view of the valve with open leaflets, FIG. 18—a top view, and FIG. 19—a cross-sectional view along line L-L from FIG. 18 of the top view that shows the interaction of the external surface of the leaflet with the rest.

The tri-leaflet heart valve prosthesis operates as follows (FIGS. 16-19). Upon opening of the valve prosthesis 1', the action of the direct flow of blood causes the turning of the leaflets 3' around an imaginary axis defined by the interaction between the bearing surfaces 9' of the leaflets 3' and the guiding surfaces 8' of the first triplet of prominences 4'. This turn occurs until equilibrium is established, the blood flowing in the forward direction, the central part of the opening 17' of the valve body 2' passing it freely and in its true. The leaflets are located practically vertically and offer no resistance to the flow. The rests 12' of the turn stops 18' of the leaflets 3' interact with the top surface 13' of the leaflets and reliably hold them in the open position. The convexo-concave making of external surfaces of the leaflets provides opening the valve even further. Upon stopping the forward flow, the leaflets 3' begin to turn and return to their original position as far as they contact each other and form in the closed position of the valve prosthesis a limited reverse flow of blood through a gap f (not shown) between the leaflets 3' and the end surface 6' of the body 2'.

INDUSTRIAL APPLICABILITY

The artificial heart valve can be industrially manufactured with the use of conventional equipment and of materials widely known and used in medicine.

When used in cardiosurgery for replacing affected natural valves, the claimed prosthesis has the following advantages:

1. It ensures high efficiency of the flow section of the valve by showing practically no resistance to the flow in the open position of the leaflets
2. It excludes the forming of congestive areas thanks to washing location areas of the turn stops and rests by the forward and reverse blood streams.
3. It significantly reduces the factor of thrombi formation.
4. It excludes the instability of the valve upon its opening thanks to making the external surfaces of the leaflets convexo-concave.
5. It excludes the falling out of the leaflets thanks to the execution of the turn stops with rests.
6. It excludes an overtravel of the leaflets under the influence of the reverse stream of blood thanks to resting the external surface of the leaflet onto the stops and the interaction of the lateral surfaces, and, consequently, it excludes regurgitation of the valve.
7. It has high reliability and life duration, good compatibility with natural tissues.

The invention claimed is:
1. A heart valve prosthesis comprising
   a ring-shaped body comprising an internal side surface defining a body opening, and end surfaces on blood down-flow and up-flow sides,
   leaflets installed on the blood down-flow end surface of the body and thus outside the body opening and adapted to turn between an open position thereof to let an entire blood flow through the body opening and a closed position to stop the blood flow, and leaflet turn stops,
the turn stops including two pairs of prominences located on the blood down-flow end surface of the body,
at least a portion of an internal surface of each one of the first pair of prominences is flat and able to interact with flat sections of the leaflets to restrict a reverse flow of blood in the closed position, the prominences being provided on opposite lateral sides thereof with guiding surfaces capable of interacting with corresponding bearing surfaces of lateral surfaces of leaflets as the leaflets open and close,
each of the guiding surfaces defined by rotating a generating line thereof relative a turning axis of the respective leaflet,
each prominence of the second pair of prominences being located opposite a part of the lateral surface of a corresponding leaflet most distant from a central surface thereof and being able to interact by its internal surface with the leaflet lateral surface part during opening of the heart valve prosthesis,
the leaflet turn stops having at least two rests capable of interacting with leaflet surfaces facing down-flow of blood in the open position, and defining a turning angle of the leaflets.

2. The prosthesis in accordance with claim 1 wherein said flat sections of the leaflets are located on the lateral surface of each leaflet from two diametrically opposite sides and have a possibility of interaction with the corresponding flat surface of the prominence of the turn stop of the leaflet in the closed position, each of said flat sections of the leaflet ending in a bearing surface, generating lines of which are inclined towards the flat surfaces, the bearing surfaces of the leaflets having a possibility of interaction with the corresponding guiding surfaces of the turn stops of the leaflets during opening and closing of the heart valve prosthesis.

3. The prosthesis in accordance with claim 1 wherein the generating lines of the guiding surface of the first pair of prominences are inclined to their internal surface, the angle of inclination corresponding to the angle of inclination of the generating line of the leaflets' bearing surface.

4. The prosthesis in accordance with claim 1 wherein the first pair of prominences is equipped with four prominences which are arranged in pairs on the internal surface of the prominences from a side facing the blood down-flow.

5. The prosthesis in accordance with claim 1 wherein the first pair of prominences is equipped with four rests arranged in pairs on the opposite lateral sides of the first pair of prominences from a side facing the blood down-flow.

6. The prosthesis in accordance with claim 1 wherein two rests of the turn stops are located on the internal surface of the second pair of prominences from side facing the blood down-flow.

7. The prosthesis in accordance with claim 1 wherein an internal surface of the opening of a ring-shaped body is shaped in a lateral surface of a circular cylinder limited by the opposite end surfaces facing the blood up- and down-flows, respectively.

8. The prosthesis in accordance with claim 7 wherein two hollows are made on the end surface facing the down-flow of blood, surfaces of each hollow serving for interaction with a part of the lateral surface of the corresponding leaflet most distant from the central surface upon opening and closing the prosthesis to thereby form a limited return flow of blood in the closed position thereof.

9. The prosthesis in accordance with claim 1 wherein a circular groove for fastening an inserted cuff is made on a lateral side of the body.

10. The prosthesis in accordance with claim 1 wherein a surface of each leaflet facing the down-flow of blood is made at least partially convex and a surface of each leaflet facing the up-flow of blood is made at least partially concave, generating lines of said convex and concave parts of the surfaces being inclined to the central surface of the leaflet.

11. The prosthesis in accordance with claim 1 wherein a surface of each leaflet facing the down-flow of blood is made at least partially convex and a surface of each leaflet facing the up-flow of blood is made at least partially concave, axes of symmetry of said parts of the surfaces being inclined to a central axis of the ring-shaped body.

12. The prosthesis in accordance with claim 10 wherein the convex and concave parts of the surfaces of the leaflets include lateral surfaces of a circular cylinder inclined relative a central axis of the heart valve prosthesis.

13. The prosthesis in accordance with claim 11 wherein the convex and concave parts of the surfaces of the leaflets.

14. The prosthesis in accordance with claim 1 wherein it is made of pyrocarbon.

15. A heart valve prosthesis comprising:
a ring-shaped body comprising an internal cylindrical side surface defining a body opening, and end surfaces on blood down-flow and up-flow sides,
three leaflets installed on the blood down-flow end surface of the body and thus outside the body opening and adapted to turn between an open position thereof to let an entire blood flow through the body opening and a closed position to stop the blood flow, and
leaflet turn stops,
wherein the turn stops include two triplets of prominences located on the blood down-flow end surface of the body,
the prominences of the first triplet of prominences having bearing surfaces on their opposite lateral sides which interact with corresponding guiding surfaces of a lateral surface of the leaflets as they open and close,
each prominence of the second triplet of prominences being located opposite a part of the lateral surface of a corresponding leaflet most distant from a central surface thereof and being able to interact by its internal surface with the leaflet lateral surface part during opening of the heart valve prosthesis,
the leaflet turn stops having at least three rests capable of interacting with the external surface of the leaflet directed to the downstream flow of blood in its open position and determining the turning angle of the leaflets.

16. The prosthesis in accordance with claim 15 wherein generating lines of guiding surfaces of the first triple of prominences are inclined to their internal surface, the angle of inclination corresponding to an angle of inclination of generating lines of bearing surfaces of the leaflets.

17. The prosthesis in accordance with claim 15 wherein the first triplet of prominences is equipped with six rests arranged in pairs on internal surfaces of the prominences from a side facing the blood down-flow.

18. The prosthesis in accordance with claim 15 wherein the first triplet of prominences is equipped with six rests arranged in pairs on opposite lateral sides of the prominences from a side facing the blood down-flow.

19. The prosthesis in accordance with claim 15 wherein three rests of the turn stops are located on internal surfaces of the second triplet prominences from a side facing the blood down-flow.

20. The prosthesis in accordance with claim 15 wherein an internal surface of the opening of a ring-shaped body is shaped in a lateral surface of a circular cylinder limited by the opposite end surfaces facing the blood up- and down-flows, respectively.

21. The prosthesis in accordance with claim 15 wherein three hollows are made on the end surface facing the down-flow of blood, surfaces of each hollow serving for interaction with a part of the lateral surface of the corresponding leaflet most distant from the central surface upon opening and closing the prosthesis, to thereby form a limited return flow of blood in the closed position thereof.

22. The prosthesis in accordance with claim 15 wherein a circular groove for fastening an inserted cuff is made on a lateral side of the body.

23. The prosthesis in accordance with claim 15 wherein a surface of each leaflet facing the down-flow of blood is made at least partially convex and a surface of each leaflet facing the up-flow of blood is made at least partially concave, generating lines of said convex and concave parts of the surfaces being inclined to the central surface of the leaflet.

24. The prosthesis in accordance with claim 15 wherein a surface of each leaflet facing the down-flow of blood is made at least partially convex and a surface of each leaflet facing the up-flow of blood is made at least partially concave, axes of symmetry of said parts of the surfaces being inclined to a central axis of the ring-shaped body.

25. The prosthesis in accordance with claim 23 wherein the convex and concave parts of the surfaces of the leaflets include lateral surfaces of a circular cylinder inclined relative a central axis of the heart valve prosthesis.

26. The prosthesis in accordance with claim 24 wherein the convex and concave parts of the surfaces of the leaflets include lateral surfaces of a circular cylinder inclined relative a central axis of the heart valve prosthesis.

27. The prosthesis in accordance with claim 15 wherein it is made of pyrocarbon.

* * * * *